United States Patent [19]

Gordon

[11] Patent Number: 4,927,260

[45] Date of Patent: May 22, 1990

[54] APPARATUS AND METHOD FOR THE PRECISION EVALUATION OF VISUAL FUNCTION IN THE FOVEA CENTRALIS (MACULA) AREA OF THE RETINA

[76] Inventor: Orville Gordon, 12915 Hunters Arrow, San Antonio, Tex. 78230

[21] Appl. No.: 255,875

[22] Filed: Oct. 11, 1988

[51] Int. Cl.$^5$ .............................................. A61B 3/02
[52] U.S. Cl. ..................................... 351/243; 351/205
[58] Field of Search ............... 351/205, 206, 211, 219, 351/222, 243, 203

[56] References Cited

U.S. PATENT DOCUMENTS 4,726,672 2/1988 O'Brien et al. ...................... 351/203

Primary Examiner—P. M. Dzierzynski
Attorney, Agent, or Firm—Andrew S. Viger

[57] ABSTRACT

A foveal vision evaluation instrument and procedure enables a precise evaluation of the visual function of the fovea centralis (macula) area of the retina. A foveal profile is developed to document the presence and state of foveal degeneration manifested by foveal segmentation and incremental changes and abnormalities in foveal vision, such as are caused by age related macular degeneration.

Beam source optics 10, beam polarization optics 20 and image selection system 30 provide a polarized projection beam PPB that transmits an image array obtained by directing one component of polarized projection beam PPB through an image transparency IT. Image element blanking optics 40 enables the individual elements of the image array to be selectively blanked using a multi-cell electro-optic shutter 45. Zoom projection optics 50 projects the image array onto a screen within the foveal field of vision, and allows the size of the projected image elements to be incrementally changed through selective control of zoom magnification with compensating brightness (contrast) adjustment through automatic control of iris setting.

11 Claims, 2 Drawing Sheets

APPARATUS AND METHOD FOR THE PRECISION EVALUATION OF VISUAL FUNCTION IN THE FOVEA CENTRALIS (MACULA) AREA OF THE RETINA

BACKGROUND OF THE INVENTION

1. Field

This invention involves an instrument for precisely measuring visual function in the fovea centralis (macula) area of the retina, and in particular, pathologic incremental changes in foveal (macular) vision caused by age related macular degeneration.

2. Problem

The fovea centralis or macula is the small central area (approximately 0.3 millimeters in diameter) of the retina that exhibits maximum visual acuity.

Many people in the senior-citizen time frame are affected by a pathological process that causes degeneration of the fovea and loss of visual function—a process typically referred to as Age-Related Macular Degeneration (AMD). AMD progresses from the loss of foveal sensitivity (i.e. reduced intensity, blur, fragmentation or other distortion), to the eventual complete loss of foveal vision. Due to increasing life-spans, more people are now vulnerable to AMD, which has become a significant source of visual disability.

AMD causes the fovea to degenerate into irregular segments that lose visual function at independently varying rates. AMD is the only foveal condition that characteristically degenerates into irregular segments of varying visual loss. Other causes of abnormalities in foveal vision result in substantially uniform loss over the whole foveal area.

Evaluating foveal degeneration caused by AMD requires detecting foveal segmentation and measuring incremental abnormalities or changes within the segments. Such evaluation is required to detect the onset and monitor the progression of foveal degeneration, thereby facilitating early and efficacious medical treatment. Moreover, without precise evaluation of foveal degeneration, judging the efficacy of experimental treatments is highly problematic.

Accordingly, the need exists for a foveal vision evaluation instrument capable of precisely evaluating foveal segmentation and degeneration, including measuring incremental abnormalities and changes in foveal visual function, as an aid to detection and treatment of AMD.

3. Prior Art.

Existing instruments for testing vision are for measuring and correcting refractive errors associated with the loss of visual acuity. AMD symptoms can be identified by observing the fovea with an ophthalmoscope; however, the observed characteristics of the diseased fovea do not correlate with visual impairment or changes in visual impairment, and cannot be used to evaluate the degeneration of foveal vision.

These instruments are not effective in evaluating the onset or progression of AMD because they cannot (a) isolate on the fovea, (b) detect foveal segmentation, or (c) monitor incremental abnormalities or changes in foveal vision. That is, they are not able to identify or locate abnormal areas throughout the foveal field of vision—abnormalities that can be localized within certain foveal segments and manifested as reduced intensity, blurring and/or fragmentation.

For example, at the standard projection distance of twenty feet, the foveal field of vision is a central area on the screen approximately fifteen centimeters in diameter. None of the available instruments is able to project an image array of letters or symbols within the foveal field of vision in order to make incremental changes in the size, presence or contrast of the image elements so as to identify and document foveal segmentation and incremental abnormalities in foveal vision.

Despite advances in knowledge of the physiology and pathology of the retina in general, practically no detailed information about the pathologic physiology of foveal degeneration has been revealed beyond the observation that victims of AMD experience degeneration in foveal vision unpredictably over a period of weeks to years until foveal vision is lost. Indeed, because of the lack of instruments for evaluating foveal vision, knowledge about foveal pathology must primarily be derived from specimen eyes.

SHORT STATEMENT OF THE INVENTION

Object of the Invention

An object of this invention is the precise evaluation of degeneration of the visual function in the foveal (macular) area of the retina by identifying foveal segmentation and incremental changes or abnormalities in foveal vision, thereby developing a foveal profile that can be used to monitor the onset and progression of foveal degeneration and the efficacy of medical treatments.

Summary of the Invention

The invention is a foveal vision evaluation instrument and procedure for precisely evaluating foveal vision and degeneration. The instrument:

(a) projects an image array of letters or symbols that is substantially within the foveal field of vision; and (b) enables incremental changes to be made in the size of the image elements based on patient responses;

thereby measuring foveal vision including any foveal segmentation and abnormalities or changes in foveal vision.

The foveal vision evaluation procedure for measuring foveal vision, and detecting the state of foveal degeneration involves:

(a) projecting into the foveal field of vision an image array of letters or symbols that are too small to be identified by the patient; and then (b) incrementally increasing the size of the image elements until the first identification can be made.

If all the image elements can be identified equally and the size is equivalent to 20/20, then foveal degeneration is not present. If any elements are not seen, or seen blurred or otherwise distorted, the procedure for measuring foveal degeneration involves:

(c) incrementally increasing the size of the image elements, observing those elements not originally seen or seen distorted; and (d) documenting the level of magnification at which those elements are seen clearly; or (e) documenting those elements remaining unseen, or the observed characteristics (e.g. reduced intensity, blur, fragmentation, distortion, flicker) of those elements never seen clearly.

The level of magnification beyond that required for normal foveal vision for any given foveal segment is the level of visual function for that segment.

For a preferred embodiment, the function of making incremental changes in the size of the image array is performed by zoom projection optics that:

(a) selectively controls the size of the projected image array elements within the foveal field by controlling zoom magnification adjustment; and (b) selectively controls the brightness of the projected image by controlling iris adjustment.

Although size and brightness adjustment can be made independently, typically these adjustments are correlated to maintain image brightness constant as image zoom magnification changes.

For a preferred embodiment, the foveal vision evaluation instrument includes an image element blanking system that selectively blanks any element in the image array to further test the effect of incremental changes on foveal vision. This function is performed by beam polarization optics and image element blanking optics. The beam polarization optics:

(a) generates two orthogonally polarized beams, denominated image and nominal;

(b) directs the image beam through an image transparency of an array of letters or symbols; and (c) recombines the image and nominal beams into a polarized projection beam that carries the image array in its image beam component.

The polarized projection beam transmits to the image element blanking optics, which includes an multi-cell electro-optic shutter formed by a multi-cell polarization rotator component (having cells that define a respective transmission path to each element of the image array) and a polarized beam selector component, that:

(d) rotates by ninety degrees the polarization of a selected portion of the polarized projection beam—both image and nominal beam components—transmitting through the cell of the polarization rotator that corresponds to the image element to be blanked; and (e) blanks the selected portion of the image beam component as it transmits through the polarized beam selector, the polarization rotation resulting in the selected portion of the image beam component being cross-polarized with the polarized beam selector.

For a preferred embodiment, the foveal vision evaluation instrument includes an image selection system that enables the projected image array to be changed. This function is implemented by providing a transparency disk containing a plurality of image transparencies (each with a defined image array) disposed around its periphery, which is rotated until a selected image transparency is positioned in the path of the image beam component of the polarized projection beam. Thus, in addition to using the image element blanking system to incrementally blank elements of a projected image array, the entire image array can be changed.

Certain Features and Advantages

Among the features and advantages of this invention are the following. An image array is projected into the foveal field of vision, allowing the visual function of the fovea to be isolated and evaluated. The image elements of the array are selectively and incrementally changed in size, allowing a precise evaluation of foveal segmentation and visual function. Selected image elements can be blanked, allowing further detailed evaluation of foveal segmentation and visual function. Adjustments to zoom magnification and iris adjustment can be correlated, allowing compensating iris adjustments to image brightness as zoom magnification is changed. Image arrays are stored in the form of image transparencies on a rotatable disk, allowing convenient and rapid selection and positioning of image arrays for projection.

The ability to project an image array of selectable size and contrast, and to selectably switch image arrays and incrementally blank elements of an array, permits precise evaluation of foveal vision ranging from normal symbol identification, to distortion of individual letters, to fragmentation, to blur, to a complete loss of visual response.

Other objects, features and advantages of this invention will be apparent from the drawings and the following detailed description of the preferred embodiment, and the appended claims.

DESCRIPTION OF THE PREFERRED EMBODIMENT

Figure 1:
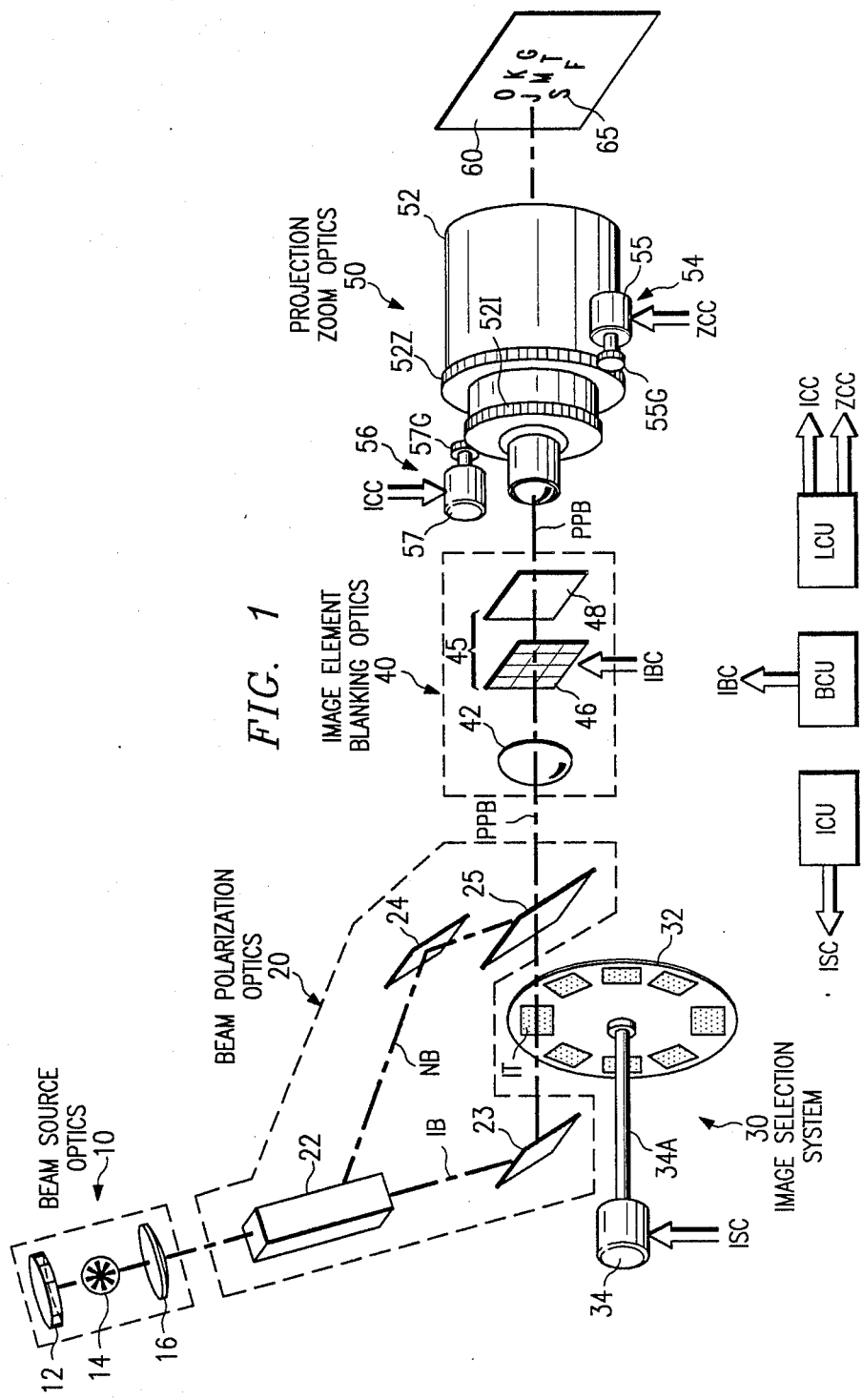
FIG. 1 is a pictorial view of the foveal vision evaluation instrument of this invention.
Figure 2:
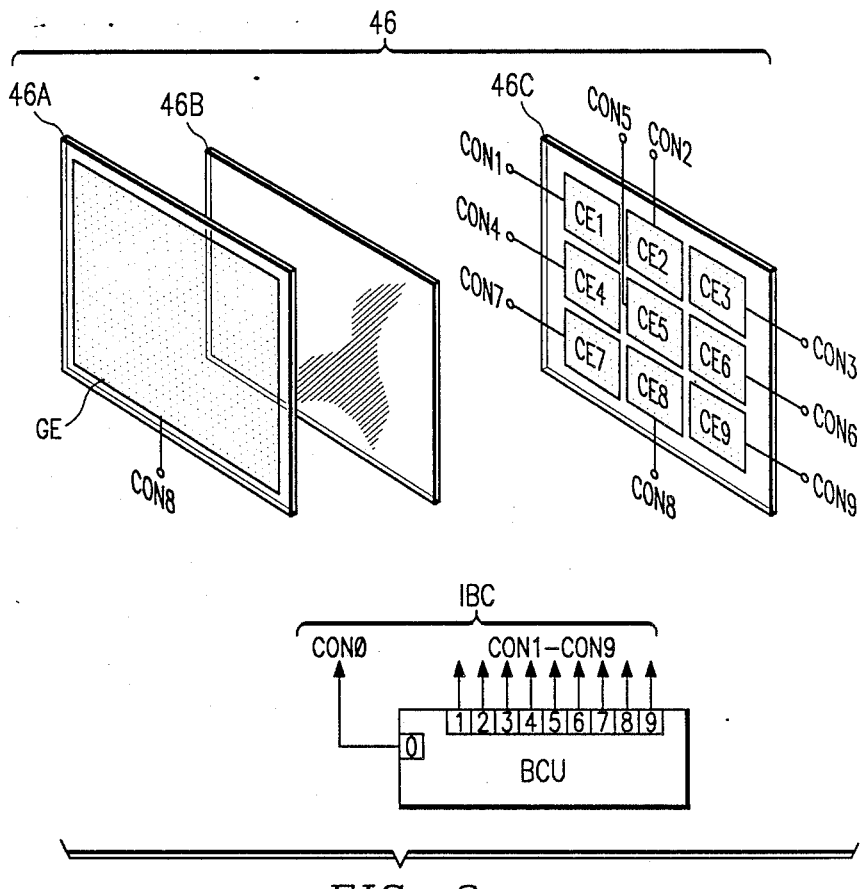
FIG. 2 is a detailed view of the polarization rotator component of the instrument.

The description of the preferred embodiment of the foveal vision evaluation instrument and procedure of this invention, which enables the precise evaluation of degeneration of visual function in the foveal (macular) area of the retina by identifying foveal segmentation and incremental changes or abnormalities in foveal vision, is organized as follows:

Source beam optics
Beam polarization optics
Image selection system
Image element blanking optics
Zoom projection optics
Foveal vision evaluation procedure
Additional embodiments Source beam optics (FIG. 1, numeral 10) generates an unpolarized source beam SB. Beam polarization optics (FIG. 1, numeral 20) splits the source beam into orthogonally polarized beams, denominated image IB and nominal NB, directs the image beam through an image transparency IT, and then recombines the image and nominal beams into a polarized projection beam PPB. Image selection system (FIG. 1, numeral 30) positions a selected image transparency IT of an image array in the path of the image beam. Image element blanking optics (FIG. 1, numeral 40) blanks selected elements of the image array by transmitting the nominal beam component and blanking the image beam component of the polarized projection beam. Zoom projection optics (FIG. 1, numeral 50) selectively controls the size and contrast of the projected image array by controlling zoom magnification and iris setting.

DETAILED DESCRIPTION

Source beam optics.

The source beam optics, shown in FIG. 1 at 10, generates an unpolarized source beam SB.

A light source 12 generates the unpolarized source beam SB. Source beam SB is condensed and collimated by a mirror 14 and a condenser lens 16.

Light source 8 may be, for example, a xenon arc lamp.

Beam polarization optics.

The beam polarization optics, shown in FIG. 1 at 20, splits source beam SB from source beam optics 10 into orthogonally polarized beams, denominated image IB and nominal NB, directs the image beam through an image transparency IT, and then recombines the image and nominal beams into a polarized projection beam PPB.

The collimated source beam SB from source beam optics 10 is directed through an orthogonal polarization element 22 that splits the source beam into two orthogonally polarized beams—an image beam IB and a nominal beam NB.

Image beam IB and nominal beam NB are respectively directed by mirrors 23 and 24, toward a beam recombiner element 25. As discussed above 4.3, image beam IB transmits through an image transparency IT upstream from the recombiner element.

Recombiner element 25 is a glass plate positioned with respect to mirrors 23 and 24 such that image beam IB is incident at the Brewster's angle for total transmission, while nominal beam NB is incident at the Brewster's angle for total reflection, causing the two beams to combine with a high degree of efficiency to provide a polarized projection beam PPB. That is, image beam IB is incident to the upstream side of recombiner element 25 at the Brewster's angle for total transmission of light of the image beam's polarization, while the orthogonally polarized nominal beam NB is incident to the downstream side of the recombiner element at the Brewsters's angle for total reflection of light of the nominal beam's polarization (the two angles of incidence being complementary).

Polarizing optical element 22 may be, for example, a Glan-Thompson prism made of calcite.

Image selection system

The image selection system, shown in FIG. 1 and 30, positions a selected image transparency IT of an image array of letters or symbols in the path of image beam IB produced by the beam polarization optics 20, upstream from recombiner element 25.

An image transparency disk 32 incorporates a plurality of image transparencies IT disposed around the periphery of the transparency disk. Each of the image transparencies IT is a substantially square 3×3 array of nine letters or symbols.

Image transparency disk 32 is coupled to a disk stepper motor 34 by an axel 34A. Disk stepper motor 34 responds to image selection commands ISC to rotate transparency disk 32 until a selected one of image transparencies IT is positioned in the path of image beam IB. The image selection commands are provided by an image transparency disk control unit ICU.

Image beam IB transmits through the selected image transparency IT, and is recombined with the orthogonally polarized nominal beam NB by recombiner element 25 to provide polarized projection beam PPB.

Image transparency disk 36 may be, for example, a properly exposed disk of disk camera film. While the preferred image array is a 3×3 array of nine letters, the image to be projected is a matter of choice. Thus, for example, images may vary in the number of elements in an array, distribution of image elements, and the size of the image elements, as well as in contrast and color.

The specification for disk stepper motor 34, and its image control unit ICU, form no part of this invention, and may be of conventional design choice. The stepper motor and its control unit should be designed to accurately position image transparency disk 32 with appropriate rapidity.

Image element blanking optics

The image element blanking optics, shown in FIG. 1 at 40, blanks selected elements of the image array carried by the image beam component of the incident polarized projection beam PPB provided by the beam polarization optics 20 and the image selection system 30, blanking the image beam component, and transmitting the nominal beam component, for the corresponding portion of the polarized projection beam.

The recombined polarized projection beam PPB is focused by a lens 42 onto an electro-optic shutter 45 comprising a multi-cell birefringent polarization rotator 46 and a polarized beam selector 48.

The multi-cell polarized rotator 46 is configured such that its cells define an array of transmission paths that correspond to the image array carried by the image beam component of the incident polarized projection beam. Polarization rotator 46 is responsive to image element blanking commands IBC to activate a selected cell, causing a ninety degree rotation in the polarization of both the image beam component IB and the orthogonally polarized nominal beam component NB of the corresponding portion of the polarized projection beam PPB transmitting through that cell. That is, after polarization rotation, the image and nominal beam components are cross polarized to their initial polarization. The image element blanking commands are provided by a blanking control unit BCU.

Figure 3:
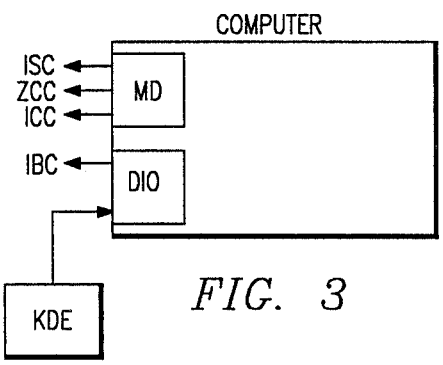
FIG. 3 is a schematic view of an instrument control computer for controlling the instrument.

As shown in FIG. 3, polarization rotator 46 is of conventional liquid crystal design comprising three layers—an electro-optic birefringent layer 46B, disposed between a front ground-electrode plate 46A and a back cell-electrode plate 46C.

Ground-electrode plate 46A comprises a transparent material (such as glass) having disposed on its interior surface a ground (or common) electrode GE. The ground electrode is formed of a transparent electrically-conductive coating material (such as indium-tin-oxide) that conducts electricity at the same time as transmitting visible light. Ground electrode GE is electrically connected to a connector CON0.

Cell-electrode plate 46C comprises a transparent material (such as glass) having disposed on its interior surface an array or grid of nine cell electrodes CE1--CE9, with each electrically-isolated cell electrode being formed of a transparent electrically-conductive coating material (such as indium-tin-oxide). Cell electrodes CE1-CE9 are electrically connected to respective connectors CON1-CON9.

The cell electrodes are arranged in a 3×3 array corresponding to the 3×3 array of the image elements—they define respective transmission paths for the corresponding portions of the image beam component IB of the incident polarized projection beam PPB. That is, incident polarized projection beam PPB transmits through polarization rotator 46 with the image element array carried by the image beam component corresponding to the cell electrode array, such that the transmission path for the portion of the image beam component associated with each image element transmits through a corresponding cell of the polarization rotator.

Electro-optic birefringent layer 46B comprises an electrooptically birefringent material (such as phenycyclohexane). A rotation voltage between ground electrode GE (the ground plane) and any of cell electrodes CE1-CE9 induces an optical half-wave effect in the corresponding portion of the birefringent layer 46B that lies between the ground electrode and the selected cell electrode. The half-wave effect produced by birefringent material 46B rotates the plane of polarization of the incident polarized projection beam ninety degrees, i.e. each of the orthogonally polarized beam components IB and NB is cross-polarized to its initial polarization direction.

To activate the polarization rotation effect, image element blanking commands IBC are applied to selected ones of conductors CON$\theta$ for the ground electrode GE and CON1–CON9 for the cell electrodes CE1–CE9. The image element blanking commands cause a rotation voltage between a selected cell electrode and the ground electrode, thereby inducing polarization rotation for the portion of the incident polarized projection beam that transmits through the portion of electro-optic birefringent layer 46B corresponding to the transmission path defined by the selected cell electrode(s). Blanking control unit BCU selectively generates the image element blanking commands.

For example, if the image element corresponding to the transmission cell defined by cell electrode CE8 is selected for blanking, an image element blanking command IBC is applied to connector CON8 resulting in a rotation voltage between cell electrode CE8 and ground electrode GE. This rotation voltage induces an optical half-wave rotation, i.e. a ninety degree polarization rotation, in the portion of the polarized projection beam PPB that transmits through cell electrode CE8. Thus, if the image beam component is assumed to be the vertically polarized, the portion of the image beam component transmitting through cell electrode CE8 would be rotated to horizontal polarization, while the corresponding portion of the orthogonally polarized nominal beam component would be rotated to vertical polarization.

As shown in FIG. 1, after the incident polarized projection beam PPB—having orthogonally polarized image and nominal beam components IB and NB—transmits through polarization rotator 46 it transmits through polarized beam selector 48 (which may be a sheet of polarized plastic. Polarized beam selector 48 is polarized in the direction corresponding to the initial polarization of image beam component IB, i.e. prior to any polarization rotation produced by polarization rotator 46. Conversely, polarized beam selector 48 is cross-polarized with the initial polarization of the nominal beam component.

Without any polarization rotation, polarized beam selector 48 transmits the image beam component of polarized projection beam PPB, and concomitantly blocks the orthogonally (i.e. cross) polarized nominal beam component. However, if one or more of the cell electrodes CE1–CE9 of polarization rotator 46 is activated by an image element blinking command IBC, the polarization rotator causes a ninety degree rotation in the polarization of that portion of each of the nominal and image beam components that transmits through the activated transmission cell. Accordingly, that portion of the image beam component for which polarization is rotated ninety degrees is now cross-polarized with and blanked by polarized beam selector 48, and the corresponding portion of the nominal beam component is transmitted, thereby blanking the corresponding image element.

The specification for the blanking control unit BCU forms no part of this invention, and may be of conventional design choice. For example, the image element blanking commands IBC may be low voltage DC signals generated by TTL logic circuits followed by operational amplifiers.

Zoom projection optics

The zoom projection optics, shown in FIG. 1 at 50, selectively controls the size and brightness of the image array carried by polarized projection beam PPB by controlling zoom magnification and iris setting.

A zoom lens 52 includes a zoom control 54 that controls the level of zoom magnification, and an iris control 56 that controls the iris setting (image brightness and contrast).

Zoom lens 52 projects the image array carried by incident polarized projection beam PPB, with selectively blanked letters, onto projection screen 60 where it is observed as a test pattern 65. The magnification of the zoom lens is selected to project test pattern 65 generally within the foveal field of vision. At the standard vision testing distance of twenty feet, the area of acute foveal vision is approximately 15 cm in diameter (the field is slightly oval, with the greatest diameter being horizontal).

In the drawing, test pattern 65 has a deleted element (corresponding to cell CE8 of polarization rotator 46) to illustrate the blanking function.

Zoom control 54 includes a zoom stepper motor 55 coupled by a coupling gear 55G to a zoom adjust ring 52Z on zoom lens 52. Zoom stepper motor 55 is responsive to zoom control commands ZCC from a zoom lens control unit LCU to control the level of zoom magnification provided by zoom lens 52, and thereby the size of the image elements in the projected test pattern 65.

Iris control unit 56 includes an iris stepper motor 57 coupled by a coupling gear 57G to an iris adjustment ring 52I on the zoom lens 52. Iris stepper motor 57 is responsive to iris control commands ICC from zoom lens control unit LCU to adjust the iris setting for zoom lens 52, and thereby the brightness (and contrast) of the projected image.

While zoom magnification can be independent of iris setting, typically the iris setting for zoom lens 52 is established by zoom lens control unit LCU such that the brightness of projected test pattern 65 remains constant with a selected level of zoom magnification. Thus, as the zoom magnification is changed by zoom control 54 in response to zoom control commands ZCC, zoom lens control unit LCU sends corresponding iris control commands ICC to iris control 56 that cause compensating adjustments to the iris setting, thereby maintaining the brightness of projected test pattern 65 substantially constant.

The specification for zoom and iris stepper motors 55 and 57, and zoom lens control unit LCU, forms no part of this invention, and may be of conventional design choice. The zoom lens control unit should be designed to include two modes of iris control—an independent mode in which iris setting is selectable independent of zoom magnification, and an automatic mode in which the zoom lens control unit provides compensating iris control commands to keep test pattern brightness substantially constant in response to selected changes in zoom magnification.

Foveal vision evaluation procedure

The above described preferred embodiment of the foveal vision evaluation instrument enables precise evaluation of foveal vision, and in particular precise evaluation of the degeneration of visual function in the fovea (macula) by identifying foveal segmentation and incremental changes or abnormalities in foveal vision.

The preferred embodiment of the foveal vision evaluation procedure involves:

(a) projecting into the foveal field of vision a selected array of image elements (letters or symbols) that are too small to be identified by the patient; and then (b) incrementally increasing the size of the image elements until the first identification can be made.

If all the image elements can be identified equally and the size is equivalent to 20/20, then foveal degeneration is not present.

However, if any elements are not seen, or seen blurred or otherwise distorted, foveal degeneration is present and the patient's description of the perceived image is documented. The procedure then is to measure foveal degeneration (including segmentation) by:

(c) incrementally increasing the size of the image elements (i.e. image array magnification), observing those elements not originally seen (or seen distorted); and (d) documenting the level of magnification at which those elements are seen clearly; or (e) documenting those elements remaining unseen, or the observed characteristics (e.g. reduced intensity, blur, fragmentation, distortion, flicker) of those elements never seen clearly.

The level of magnification beyond that required for normal foveal vision for any given foveal segment, i.e. any element of the image array, is the level of visual function for that segment. Foveal segments in which vision remains distorted or blurred have experienced severe loss of visual function, while segments that remain blank have completely lost visual function.

In the course of this procedure for evaluating foveal degeneration using incremental changes in image array magnification, the effect of other incremental changes in the test pattern can be investigated by:

(f) blanking selective image elements to observe the effect on foveal vision in other foveal segments, or to isolate a foveal segment; and/or (e) changing the entire image array by selecting a different image transparency IT.

Using the foveal vision evaluation procedure to evaluate foveal degeneration, a foveal or macular profile can be developed that documents the foveal segments and the visual function in each segment. Such a profile can then be used to determine whether medical treatment is advised, and if so, to select an appropriate treatment and evaluate its efficacy.

Additional embodiments

While the foveal vision evaluation instrument, and a foveal vision evaluation procedure, have been described in connection with a preferred embodiment, other embodiments within the spirit and scope of the invention as defined by the following claims will be apparent to those skilled in the art.

For example, the intensity of the background light can be varied, and/or background color can be introduced. An image array may be replaced by a non-elemental pattern or design, with the evaluation procedure focusing on segmentation and/or distortion (eg. blur, fragmentation) of the pattern or design.

Also, the foveal vision evaluation instrument and procedure can be adapted to computerized control of certain functions. For example, computer control functions can include programming an appropriately configured computer to:

(a) implement the functions of the image control unit ICU, the blanking control unit BCU and the zoom lens control unit LCU in respectively providing the image selection commands ISC, the image element blanking commands IBC and the zoom and iris control commands ZCC and ICC, either in response to examiner input or automatically (such as to provide automatically iris control commands to compensate for changes in zoom magnification;

(b) implement selected aspects of the foveal evaluation test procedure (such as changing image size and blanking image elements);

(c) document and store for future comparison foveal profiles; and (d) perform statistical analyses on the results of the evaluation procedure to evaluate foveal degeneration including segmentation and visual abnormalities and prepare a foveal profile.

As shown in FIG. 3, an instrument control computer is configured with (a) a motor driver board MD that provides image selection control commands ISC, and zoom and iris control commands ZCC and ICC, and (b) a digital I/O board DIO that provides image element blanking commands IBC. The digital I/O board also provides an interface for a digital data entry keypad KDE that can be operated by an examiner to enter patient responses.

In this configuration, the computer with motor driver board MD and digital I/O board DIO replaces image control unit ICU, zoom lens control unit LCU, and image element blanking control unit BCU. The motor driver board MD and the digital I/O board DIO are of conventional design and are commercially available.

The computer can be programmed to implement the following foveal vision evaluation procedure. The computer issues an image selection command ISC to image transparency disk stepper motor 34, selecting an image array transparency. A zoom magnification control command ZCC and a corresponding iris setting control command ICC are respectively directed to the zoom and iris stepper motors 55 and 57, setting the image array size and brightness. The examiner queries the patient and enters on the data entry keypad KDE the patient's responses to reading the projected test pattern. The computer then issues zoom and iris control commands ZCC and ICC to change image element size (with image brightness remaining constant) and/or issues an image element blanking command IBC to the polarization rotator to blank a selected image element(s).

The computer accumulates the responses during the course of the evaluation procedure. At the end of the evaluation procedure, the responses are statistically analyzed to compute a foveal vision profile.

I claim:

1. A foveal vision evaluation instrument for evaluating visual :unction in the foveal (macular) area of the retina, comprising:

(a) Foveal test image means for projecting an image that is substantially within the foveal field of vision;

(b) image magnification means for controlling the magnification of the image within the foveal field and (c) foveal vision measurement means for controlling said image magnification means to incrementally change image magnification within the foveal field based on patient responses indicative of the patient's foveal vision function;

thereby measuring foveal vision including any degeneration in foveal vision function such as is manifested by foveal segmentation and abnormalities or changes in foveal vision.

2. The instrument defined in claim 1 wherein the image mangification means comprises: zoom projection optics means for selectively controlling the size and brightness of the projected image, either independently or such that image brightness remains substantially constant with changes in image size.

3. The instrument defined in claim 2 wherein the zoom projection optics comprises:
   (a) a zoom lens including zoom magnification optics and an iris;
   (b) zoom magnification control means for selectively controlling the zoom magnification optics to change the size of the projected image; and
   (c) iris control means for selectively controlling the iris to change the brightness of the projected image.

4. The instrument defined in claim 3 wherein the zoom mangification control means and the iris control means comprises: respective stepper motors responsive to respective zoom and iris control commands to respectively control the zoom magnification optics and the iris.

5. The instrument defined in claim 1 wherein the projected image comprises: an array of image elements (letters or symbols).

6. The instrument defined in claim 5 further including: an image element blanking means for selectively blanking any element in the image array.

7. The instrument defined in claim 6 wherein: the image projection means generates a projection beam that transmits the image.

8. The instrument defined in claim 7 wherein the image element blanking means comprises:
   (a) multi-cell electro-optic shutter means responsive to image element blanking commands for selectively blanking the elements of the image array;
   (b) each cell of the shutter means defining a transmission path for a corresponding portion of the projection beam associated with an element of the image array.

9. The instrument defined in claim 8 wherein the image projection means comprises:
   (a) source beam means for generating an unpolarized source beam;
   (b) beam polarization means for splitting the unpolarized source beam into two orthogonally polarized beams, denominated image and nominal, and then recombining the image and nominal beams into a polarized projection beam;
   (c) image selection means for positioning an image transparency of an image array in the path of the image beam prior to recombining with the nominal beam;

and wherein the multi-cell electro-optic shutter comprises;
   (d) multi-cell polarization rotator means responsive to the image element blanking commands for selectively inducing a polarization rotation of substantially ninety degrees in the transmission cell through which transmits a corresponding portion of the polarized projection beam (including the image and nominal beam components) associated with an element of the image array; and
   (e) polarized beam selector means for transmitting a beam polarized in the initial direction of polarization for the image beam component of the polarized projection beam and blanking a cross-polarized beam.

10. A foveal vision evaluation procedure for evaluating visual function in the foveal (macular) area of the retina, comprising the steps of:
    (a) projecting into the foveal field of vision an image array of elements (letters or symbols) that are too small to be identified by the patient; and then
    (b) incrementally increasing the size of the image elements until the first identification can be made;
    (c) documenting the observation of the patient; and then, if any image elements are not seen clearly,
    (d) incrementally increasing the size of the image elements, observing those elements not seen clearly; and
    (e) documenting the observation of the patient as the image elements are increased in size, thereby evaluating foveal visual function.

11. The foveal vision evaluation procedure defined in claim 10, further comprising the steps of:
    (a) selectively blanking the elements in the image array; and
    (b) documenting the observation of the patient as the elements are blanked, thereby evaluating foveal segmentation.

* * * * *